United States Patent
Shchervinsky

(12) 
(10) Patent No.: US 6,893,424 B2
(45) Date of Patent: May 17, 2005

(54) DRAIN CATHETERS

(76) Inventor: Semyon Shchervinsky, 6 Menlo Dr., Whitehouse Station, NJ (US) 08889

( * ) Notice: Subject to any disclaimer, the term of this patent is extended or adjusted under 35 U.S.C. 154(b) by 423 days.

(21) Appl. No.: 10/265,962

(22) Filed: Oct. 7, 2002

(65) Prior Publication Data

US 2004/0006311 A1 Jan. 8, 2004

Related U.S. Application Data

(63) Continuation-in-part of application No. 10/189,216, filed on Jul. 4, 2002.

(51) Int. Cl.⁷ ............................................. A61M 25/00
(52) U.S. Cl. ..................................................... 604/264
(58) Field of Search ............................... 604/43, 164.1, 604/29, 322, 272, 266, 540, 543, 541, 264; 606/184, 185

(56) References Cited

U.S. PATENT DOCUMENTS 4,398,910 A * 8/1983 Blake et al. ................ 604/266
5,116,310 A * 5/1992 Seder et al. ................. 604/43
5,360,414 A * 11/1994 Yarger ......................... 604/264
6,206,849 B1 * 3/2001 Martin et al. ............... 604/264
6,478,789 B1 * 11/2002 Spehalski et al. ........... 604/264

* cited by examiner

*Primary Examiner*—Kevin T. Truong

(57) ABSTRACT

The present invention is directed to a wound drain catheter system for draining fluid from, or supplying medication to, a wound in a patient. The system comprises (A) a trocar having (a) a blade portion on a distal end; and (b) a connector portion on a proximal end, the connector portion being a hollow core lying on a longitudinal axis; (B) a drain having (a) a first connector portion on a distal end, the first connector portion being a protrude lying on a longitudinal axis; and (b) a second connector portion on a proximal end; (C) a flexible outflow tube having (a) a proximal end and a distal end; and (b) a smooth exterior for sealing to surface tissue at the point of exit from the body of a patient; and (D) means for connecting the second connector portion of the drain to the distal end of the flexible outflow tube. The protrude of the first connector portion of the drain engages the interior of the hollow core of the connector portion of the trocar. The wound drain catheter system may also include a bioabsorbable transitional part.

18 Claims, 12 Drawing Sheets

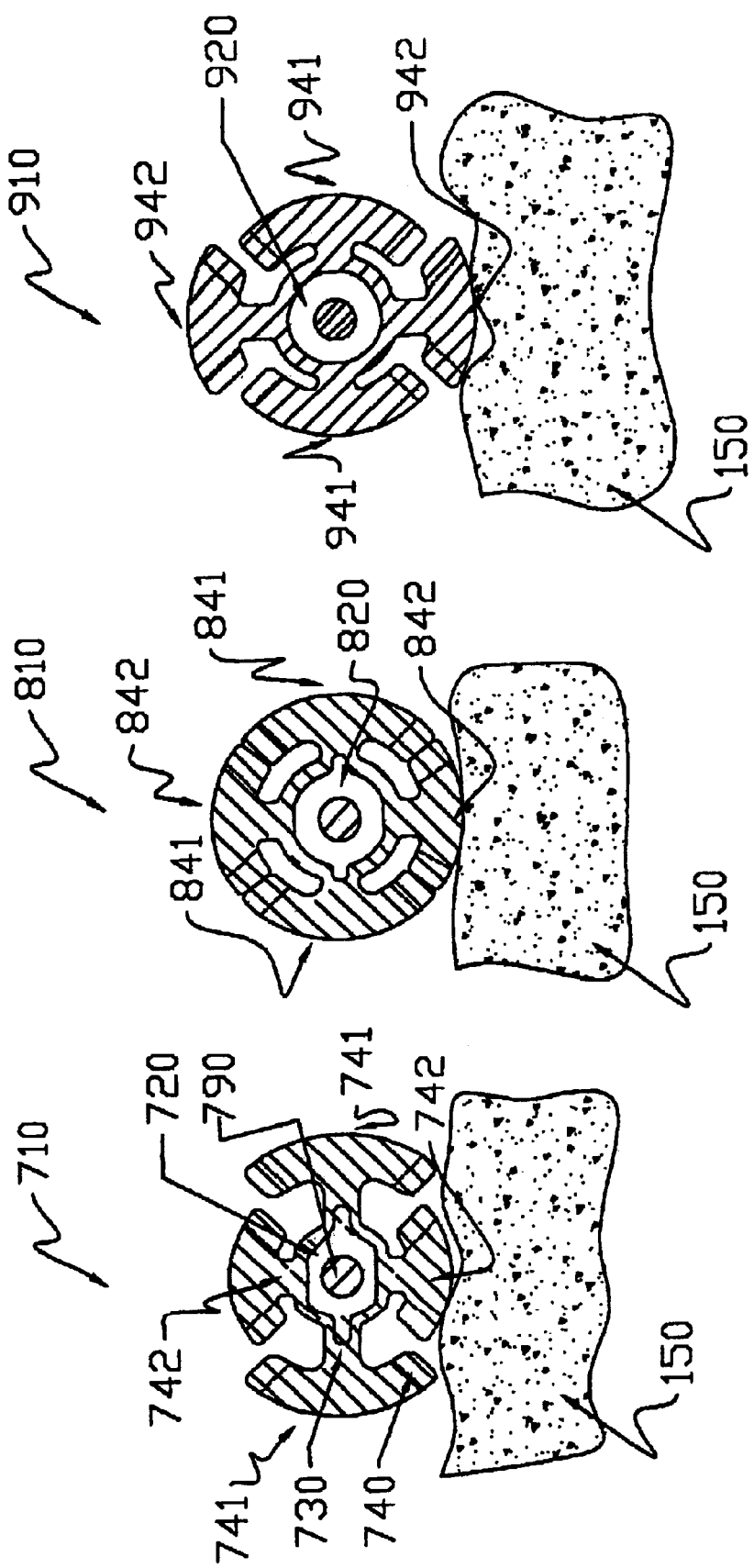

DRAIN CATHETERS

This application is a continuation-in-part of application Ser. No. 10/189,216, filed Jul. 4, 2002.

FIELD OF THE INVENTION

The present invention relates to multilumen wound drain catheters for removing fluids from a wound. The present invention also relates to trocars to be used with wound drain catheters. The wound drain catheters and trocars may also be used to supply medication to, and balance gas pressure in, a wound.

DESCRIPTION OF THE BACKGROUND

Wound drain catheters for draining closed wounds generally comprise a drain portion in fluid communication with a wound and an outflow tube for transporting fluid from the drain to a reservoir. Typically, the outflow tube is connected to a vacuum source after the drain has been placed in the wound and the wound has been closed. The most common type of wound drain catheter is a tubing perforated with spaced apertures through the tubing wall. The spaced apertures are usually in opposed pairs and the spacing between the aperture pairs may vary. A significant problem with wound drain catheters is that wound debris, such as clots, may block the apertures thereby reducing the effectiveness of the drain. Another problem is that as the wound heals, tissue tends to form in the apertures of the wound drain catheter further reducing the effectiveness of the drain. In addition, when the wound drain catheter is removed from the patient, such as by applying a pulling force, any tissue that has grown into the apertures will be torn from the patient's body causing discomfort and retarding the healing process. If tissue growth into the apertures is extensive, the drain may break during removal thereby leaving a portion of the drain in the patient's body requiring additional surgery.

Other wound drain catheters have flat or round elongated channel shapes with a solid core, however, these channels tend to easily collapse. Furthermore, when these drain catheters are removed such as by pulling, the diameter of the catheter decreases and gaps between channels causes pinching thereby trapping tissue during drain removal.

Wound drain catheters generally have a flexible drain portion and a flexible outflow tube portion. The drain portion is integral or attached to the outflow portion. The drain portion is placed in or adjacent the wound site and the outflow portion will pass through the skin of the patient and be connected to a source of vacuum to drain the wound site.

Trocars are commonly used to insert wound drainage catheters or tubing into a drainage site adjacent a surgical wound or from a surgical wound site through the skin of a patient. These trocars usually have the tubing attached to the one end of the trocar so that the tubing follows the trocar along a path through the patient's body. The trocars are usually made of surgical grade stainless steel or other materials so that they may be sharpened to a very fine point to allow the distal end (end farthest from the point of origin) or sharpened end of the trocar to pass through the body tissue. There is generally a slight bend, about 15 degrees, in the trocar to allow the trocar to be manipulated through the body of the patient to correctly position the wound drainage tubing in the position desired by the surgeon. In many instances, it is difficult to properly position the wound drainage tubing because it is difficult to pass the trocar through the patient's body without hitting a solid structure such as bone.

Several techniques may be used to insert a wound drain catheter in the patient's body. For example, a surgeon may simply place the drain portion and a small part of the outflow tube portion in the wound, close the incision, and suture around the outflow tube portion. This technique is somewhat unsatisfactory, since it is difficult to completely seal the area around the outflow tube by suturing, and thus, the wound may become infected. A more satisfactory technique is to pass a trocar, preattached to the end of the outflow tube, through healthy tissue by entering the patient's body at a point within the wound and exiting at a point adjacent to the wound. The surgeon pulls the trocar with the outflow tube portion through the tissue until the catheter is properly positioned, with the drain in the wound. Since the outflow tube exits the body at a point adjacent the wound, the wound can be completely closed by suturing, thereby reducing the risk of infection.

U.S. Pat. No. 3,136,316 (Beall) discloses a catheter comprising a tubular body having a longitudinally extending passage. A distal marginal end of the tubular body has at least two longitudinally extending grooves. At least one aperture provides communication between the passage and each of the longitudinal grooves. At least two longitudinally extending rows of a plurality of segmental grooves on the periphery of the tubular body provide liquid communication with the longitudinally extending grooves. The grooves of the one row are longitudinally offset from the grooves of the other row.

U.S. Pat. No. 3,407,817 (Galleher, Jr.) discloses a catheter comprising a tube of elongated configuration adapted to be inserted in a body passageway and having a main bore opening through the end of the tube. A through passage extending longitudinally within the wall of the tube is provided having plug means inserted adjacent one end of the tube to seal the passage. An inflatable cuff encircles the tube at a position near the one end of the tube. The tube passage has communication through the wall of the tube adjacent the plug means with the interior of the inflatable cuff. Cuff inflation means is inserted in the passage near the opposite end of the tube. The inflating means has a pressure release opening. A resilient means is removably secured over the opening. The resilient means in the scaling relation indicates the extent to which the cuff is inflated in response to fluid pressure from the inflating means. The resilient means when removed from the scaling relation simultaneously deflates itself and the cuff.

U.S. Pat. No. 3,590,820 (Nehru) discloses a hollow cylindrical aspirator tip that has radially passages that communicated hollow cylindrical tip with the outer ends of the longitudinal extending slot passages. Specifically, Nehru discloses an aspirator tip comprising a hollow cylindrical member having one closed end. Radially extending primary passages are provided through the aspirator tip adjacent the closed end. Means operably associated with the primary passages for relieving vacuum drawn in the primary passages to prevent damage to mucous membrane in contact with the aspirator tip over the outer end of the primary passages there through on drawing a vacuum through the tip are also included. Longitudinally extending relief passages in the tip communicating are included with the primary passages. Longitudinally extending slots between the exterior surfaces of the tip and the relief passages in the tip are also included to permit drawing of fluid through the slots into the relief passages and subsequently into the interior tip through the primary passages. This type of drain is limited in use and is specifically designed to remove blood and secretion during a surgical incision, whereby the tip is connected to a high vacuum source.

U.S. Pat. No. 3,599,641 (Sheridan) discloses a multilumen catheter having a proximal end, a distal end adapted for insertion in the body of a patient, and a principal channel connecting the distal end with the proximal end for transport of fluid. A secondary channel of smaller size than the principal channel is provided, An opening through the sidewall of the catheter adjacent the proximal end provides fluid flow across to the secondary channel and a connector tube of smaller outside diameter than the catheter fixed at one end to the opening. A combination connector channel closure system for the catheter comprises a first connector member having an enlarged central body portion. A male connector portion on one end and a female portion at the opposite end into which the proximal end of the catheter fixed is also provided. A second connector member of similar configuration to the first connector member is fixed at the female portion to the free end of the connector tube. A short section of flexible plastic tubing is fitted at one end over the male connector portion of the first connector member and is fitted at the other end over the male connector portion of the second connector member. The combination of short tubing and connector members forms a resealable seal against entrance of material into the catheter and the connector tube.

U.S. Pat. No. 3,630,206 (Gingold) discloses a bladder catheter for males having an elongated flexible core element having first and second end portions and an outer surface provided with one or more grooves extending along the core element at the first end portion of the core element for being received and retained within the bladder of a subject to be treated. A flexible tubular member within an opening is slidably received about the core element. After the element with its tubular member about it are inserted into the urethra of the subject with the first end portion of the core element received and retained within the bladder, the tubular member is partially withdrawn from about the core element to an extent allowing the urethra to be flushed by the draining urine while still remaining in position over the second end portion of core element to receive the urine into the tubular member for external disposal. This type of drain is limited in use and is specifically designed to flush the urethra, is not for use in post-surgical drainage, and is always exposed to infection.

U.S. Pat. No. 3,860,008 (Miner et al.) discloses a surgical drain comprising a series of rods lying on two horizontal planes. The rods of one plane are staggered in relation to the rods on the other plane. The rods on the same plane are in spaced relation to each other and the rods on the plane are connected to adjacent rods on the other plane by a web. The drain is adapted to be torn along a web on a line substantially parallel to a rod and adjacent rods are in acute angular relation to each other. This type of drain has a limit of use and is specifically design to the atmosphere, rather than to an outflow tube and being exposed to infection.

U.S. Pat. No. 4,398,910 (Blake et al.) discloses a wound drain catheter for draining fluid form, or supplying medication to, a closed, deep wound having a drain. The drain comprises a core portion having a longitudinal axis. Plural strut portions are provided extending outwardly from the core portion. Overhang portions, connected to the outward ends of the strut portions, respectively, cooperate with the strut portions to form longitudinal lumens. The overhang portions cooperate with each other to form, on the outer surface of the drain, the segments of a segmented, closed curve. The gaps between the segments provide plural longitudinal grooves for fluid communication between the wound and a respective one of the plural lumens. The grooves are sized to inhibit tissue from growing and debris from passing through. The drain is formed of a material which, when placed in tension between the gripping wound tissue and a force used to withdraw the drain from the wound, will reduce sufficiently in cross section to reduce the gripping force to facilitate withdrawal. The drain has a substantially uniform cross section throughout the portion of its length which is placed in tension during such removal to provide means for reducing stress risers and thus preventing breakage. A flexible outflow tube has a smooth exterior for sealing to surface tissue at the point of exit from a patient's body. Means conforming to the segmented, closed curve, for connecting the outflow tube to the drain are also provided.

U.S. Pat. No. 4,445,897 (Ekbladh et al.) discloses a catheter for post surgical drainage of a wound comprising a flexible tube having a distil end and a proximal end. The catheter has a centrally arranged inner lumen that extends longitudinally. The catheter is adapted to be connected at its proximal end to a suction means for withdrawing drainage through the lumen and is adapted for its distal end to be implanted in the wound area to be drained. In the catheter, there is provided at least one longitudinal slot opening in the surface of the distal end of the catheter which connects to a second longitudinal lumen which is at least as long as the slot opening and has a maximum width which is larger than the width of the slot opening. There is further a plurality of through openings extending between the base of the second lumen into the first lumen, whereby drainage can pass from the wound area to the second lumen then into the first lumen.

U.S. Pat. No. 4,465,481 (Blake) discloses an elongate catheter of one piece construction for draining fluid from or supplying fluid to an environment comprising a drain segment of substantially constant cross section throughout its length having plural elongate fluid openings in the form of grooves extending throughout the length of the sidewall. The openings are spaced circumferentially from one another. A second transition segment is provided with closed sidewalls in fluid communication with the elongate openings of the drain segment having an perimeter size, in cross section, substantially the same as that of the drain segment, but having an interior cross section different from that of the drain segment.

U.S. Pat. No. 5,549,579 (Batdorf et al.) discloses a drainage tube having a proximal end and a distal end including an implantable portion adapted for implantation beneath the skin of a patient. The implantable portion has a length and comprising in combination: (a) a hollow tubular collecting portion having a first length, a first outer surface and a first inner surface having struts projecting inward therefrom coextensive with the first length, the first outer surface presenting a uniform first cross-sectional profile along the first length and wherein the first cross-sectional profile has a greatest dimension; and (b) a hollow tubular extension portion having a second length and a second outer surface having a substantially uniform second cross-sectional profile coextensive with the second length, the second cross-sectional profile having a greatest dimension which is less than the greatest dimension of the first cross-sectional profile; and (c) a hollow transition portion therebetween, the transition portion providing an integral connection between the proximal end of the collecting portion and the distal end of the extension portion, the transition portion providing a gradual transition between the first cross-sectional profile and the second cross-sectional profile; the improvement wherein the greatest dimension of the first cross-sectional profile and the greatest dimension of the second cross-sectional profile of the implantable portion of the drainage tube progressively decreases along the length of the implantable portion in the direction of the proximal end of the drain, and wherein the implantable portion is of unitary construction.

U.S. Pat. No. 6,099,513 (Spehalski) discloses a wound drain device for implantation into and for drainage of fluid from a wound of a patient. The device comprises an elongated annular outer wall defining an exterior surface. An elongated central core defining at least one longitudinal axis is provided and is disposed within and spaced radially inwardly from the outer wall. A plurality of elongated radial inner walls is disposed within the outer wall and extends along, outwardly from, and circumferentially spaced about the longitudinal axis. The inner walls further extend between and connect to the central core and the outer wall such that the inner walls together with the outer wall form a plurality of elongated enclosed lumens for draining fluids from the wound. The lumens circumferentially are spaced from one another about and extend along the longitudinal axis such that the inner walls are disposed between the lumens. Each of the inner walls has an elongated open duct defined and extend along the longitudinal axis such that each of the ducts is in a respective one of the inner walls disposed between the lumens. Each of the ducts is formed by an interior base surface defined in the respective one inner wall adjacent to the central core and by a pair of opposing interior side surfaces defined in the respective one inner wall so as to extend from the interior base surface to the exterior surface of the outer wall and define an elongated entrance to the duct through the outer wall to permit fluid flow from the wound exteriorly of the outer wall through the entrance and into the duct. Each of the ducts has a maximum width between the opposing interior side surfaces which is substantially smaller than a maximum width of each of the lumens between the inner walls. This type of drain has limited use and is specifically design to the atmosphere, rather than to an outflow tube and always exposed to infection causing organism. This type of drain can be easily clogged in the entrance passage area and is closed the drain communication at the entirely lumen (slot) length.

Prior art wound drain catheter systems typically suffer from one or more problems. The systems may be rigid, bulky, difficult to use, have limited use, have permanent attachments, and may not eliminate the risk of infection. Optimally, the drains should be brought out through an incision in healthy tissue and not through an incision in the wound. A drain tract coming through the suture line increases the risk of infection and is a potential source of weakness that may lead to ventral hernia. Percutaneous catheter drainage is recommended for all postoperative trauma patients. The drains are generally anchored to the skin with a nonabsorbable suture and the use of sterile safety pins prevent retraction of the drains into the wound. At present, catheters are fastened in position either by suturing the catheter to the skin or by using adhesive tape. Adhesive tape tends to become wet as a result of the discharge of body fluids and thus loses adhesion. Sutures can be inadvertently placed around or through drains causing the drains to break off inside the body. Accordingly, there is a need for an improved method of introducing a percutaneous wound catheter.

IN THE FIGURES

FIG. 7 is a lateral cross-sectional view of the drain catheter shown in FIG. 4 in relationship to a wound. The shape of the drain catheter is shown when the pressure in the hollow core is at one atmosphere.

FIG. 8 is a lateral cross-sectional view of the drain catheter shown in FIG. 7 in relationship to a wound. The shape of the drain catheter is shown when the pressure in the hollow core is increased above one atmosphere.

FIG. 9 is a lateral cross-sectional view of the drain catheter shown in FIG. 8 in relationship to a wound. The shape of the drain catheter is shown when the pressure in the hollow core is at maximum pressure.

SUMMARY OF THE INVENTION

Figure 1:
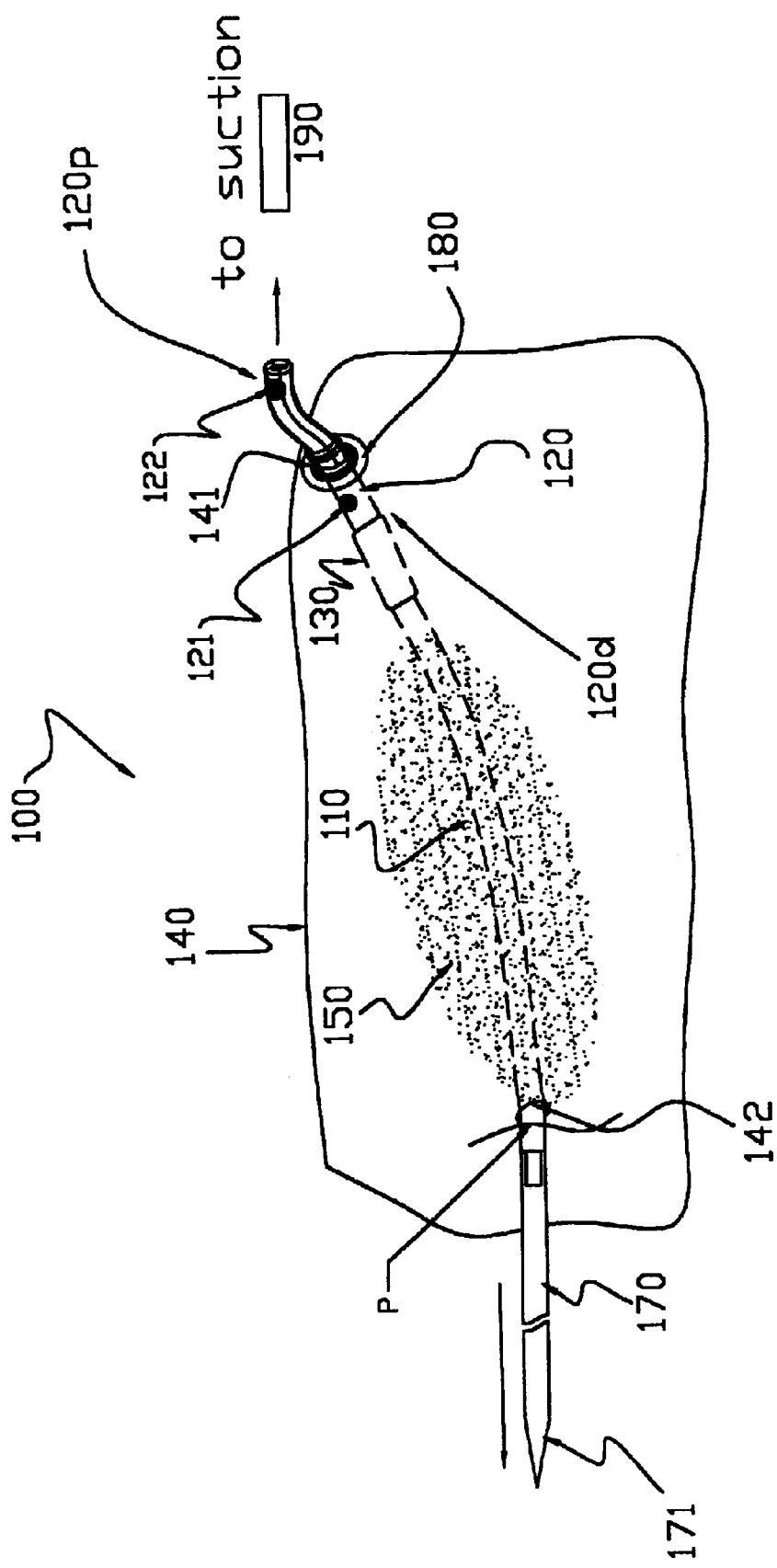
FIG. 1 is a schematic drawing of a wound drain catheter of the present invention placed in a closed, deep wound showing the drain portion and part of the outflow tube in the body of the patient.

The present invention pertains to a wound drain catheter for draining fluid from, or supplying medication to, a wound in a patient comprising:
(A) a drain comprising:
  (a) a hollow core having a longitudinal axis;
  (b) plural struts extending outwardly from the hollow core and being closed to the hollow core; and
  (c) plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough;
(B) a flexible outflow tube having a smooth exterior for sealing to surface tissue at the point of exit from the body of a patient; and
(C) means conforming to the segmented, closed curve for connecting the drain to the flexible outflow tube.

The present invention also pertains to a method for draining fluid from, or supplying medication to, a wound in a patient comprising:
(1) providing a drain catheter having a flexible outflow tube;
(2) placing the drain catheter and the flexible outflow tube in the wound of a patient;
(3) closing the wound to seal the wound from the atmosphere;
(4) connecting the flexible outflow tube to a reservoir; and
(5) removing the drain catheter from the wound by applying a tensile force;
wherein the drain catheter comprises:
(A) a drain comprising:
  (a) a hollow core having a longitudinal axis;
  (b) plural struts extending outwardly from the hollow core and being closed to the hollow core; and
  (c) plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough;
(B) a flexible outflow tube having a smooth exterior for sealing to surface tissue at the point of exit from the body of a patient; and
(C) means conforming to the segmented, closed curve for connecting the drain to the flexible outflow tube.

The present invention also pertains to a wound drain catheter system for draining fluid from, or supplying medication to, a wound in a patient comprising:
(A) a trocar having:
  (a) a blade portion on a distal end; and
  (b) a connector portion on a proximal end, the connector portion being a hollow core lying on a longitudinal axis;
(B) a drain having:
  (a) a first connector portion on a distal end, the first connector portion being a protrude lying on a longitudinal axis; and
  (b) a second connector portion on a proximal end;
(C) a flexible outflow tube having:
  (a) a proximal end and a distal end; and
  (b) a smooth exterior for sealing to surface tissue at the point of exit from the body of a patient; and
(D) means for connecting the second connector portion of the drain to the distal end of the flexible outflow tube;
wherein the protrude of the first connector portion of the drain engages the interior of the hollow core of the connector portion of the trocar.

The present invention further pertains to a wound drain catheter system for draining fluid from, or supplying medication to, a wound in a patient comprising:
(A) a trocar having:
  (a) a blade portion on a distal end; and
  (b) a connector portion on a proximal end, the connector portion being a hollow core lying on a longitudinal axis;
(B) a bioabsorbable transitional part having:
  (a) a first connector portion on a distal end, the first connector portion being a protrude lying on a longitudinal axis;
  (b) a connector portion on a proximal end, the connector portion being a hollow core lying on a longitudinal axis; and
  (c) a stop portion being substantially perpendicular to the longitudinal axis of the bioabsorbable transitional part;
(C) a drain having:
  (a) a first connector portion on a distal end, the first connector portion being a protrude lying on a longitudinal axis; and
  (b) a second connector portion on a proximal end;
(D) a flexible outflow tube having:
  (a) a proximal end and a distal end; and
  (b) a smooth exterior for sealing to surface tissue at the point of exit from the body of a patient; and
(E) means for connecting the second connector portion of the drain to the distal end of the flexible outflow tube;
wherein the protrude of the first connector portion of the drain engages the interior of the hollow core of the connector portion of the bioabsorbable transitional part and the protrude of the bioabsorbable transitional part grippingly engages the interior of the hollow core of the connector portion of the trocar.

DETAILED DESCRIPTION OF THE INVENTION

The term "proximal", as used herein, means that portion of the wound drain catheter, or element thereof, which is in close proximity to the external source of vacuum. Conversely, the term "distal", as used herein, means that portion of the wound drain catheter, or element thereof, which is furthest from the external source of vacuum.

The present invention comprises a wound drain catheter for draining fluid from, or supplying medication to, a wound in a patient. The drain of the present invention provides an increased tissue contact drainage area and an increased lumenal flow drainage area compared to prior art drains. Further, the specific configuration of this wound drain catheter provides an increased drain body cross-sectional area and eliminates weak points in the drain body. This configuration makes the wound drain catheter of the present invention stronger than comparably sized drains and therefore less likely to break during removal. Moreover, the present drain configuration reduces the risk that tissue growth will inhibit removal of the drain. Thus, the drain provides safety, reliability, and effectiveness not found in prior art drains.

The wound drain catheters of the present invention are fluted and comprise a hollow central core with radially projecting strut portions. The radial strut portions may or may not be of equal size and may or may not be spaced at equal angles relative to each other. An overhang portion extends from the end of each strut portion to form T-shaped members. These overhang portions form the periphery of the wound drain. The overhang portions and strut portions together form channels or lumens which extend throughout the length of the wound drain catheter. When viewed from a lateral cross-sectional angle, the overhang portions form a segmented circle having gaps between adjacent overhang portions. These gaps extend longitudinally throughout the length of the drain and form grooves which permit fluid entry into the lumens. The grooves that do not have direct contact tissue may have a width of about 0 to 0.3 times the diameter of the drain.

The hollow tube portion may be inflated or deflated to accommodate the draining process. This is especially important during removal of the wound drain catheter. Inflating the wound drain catheter prior to removing it with a strong pulling force counters the tendency of the wound drain catheter to decrease in diameter when pulled and thereby minimizes pinching and the subsequent trapping of any tissue that has grown into the drain during drain removal.

The hollow core of the wound drain catheter may be filled with biocompatible liquids or gases or combinations of both. The hollow core of the wound drain catheter may also be filled with one or more biocompatible springs. The filler material can be preset inside the hollow core for atmospheric pressure, for example, and then a doctor can change pressure inside the hollow core for higher or lower pressure, or pulsation. When the pressure in the hollow core is increased, the groves are opened and the effectiveness of the drain process is better than at ambient pressure. In addition, when the pressure is increased inside the hollow core, the groves are opened such that embedded tissue slides out from the catheter grove structure without ripping the tissue. As the doctor removes the drain, the pulling force causes the wound drain catheter to "neck down", or reduce in cross-sectional area, along its length, thereby relieving the gripping force of the tissue and permitting the drain to be more easily removed. The different levels of pressure in the hollow core help control the effectiveness of the drain process and eliminates tissue trauma during removal of the drain catheter from the patient.

The overhang portions form the periphery of the wound drain and may optionally have spaced apertures on the outward ends of the overhang portions. The spaced apertures may or may not be of equal size and may or may not be spaced at equal distances relative to each other. The spaced apertures provide additional fluid entry into the lumens, especially in the case when the slot is closed or collapsed.

One or more constraint sutures or wires may optionally be included inside the hollow core portion, the lumen, or even in the solid strut portion or overhang portion. A first end of the constraint suture or wire may be attached to a proximal end of the drain and a second end of the constraint suture may be attached to a distal end of the drain or to the flexible outflow tube. In this way, the constraint suture or wire provides additional cross-sectional strength and prevents breakage of the drain during removal. The use of constraint sutures or reinforcing wires also permits the use of a smaller diameter and more pliable drain system with thinner walls without decreasing the strength of the catheter. The use of constraint sutures also prevents the wound drain catheter from excessively "necking down". The hollow core with filler, or with constrain sutures and apertures on the slots, also makes the drain catheter more pliable and more effective with fluid evacuation (minimizing collapse of vacuum entries) compared to compared to solid core catheters.

The invention will be better understood from the following detailed description of the preferred embodiments taken in conjunction with the Figures, in which like elements are represented by like referenced numerals.

FIG. 1 is a schematic drawing of the wound drain catheter in a preferred embodiment of the present invention. The drain and part of the outflow tube are placed in a closed, deep wound in the body of a patient. In FIG. 1, the wound drain catheter is depicted generally as 100 and is constructed in accordance with a preferred embodiment of the present invention. The wound drain catheter 100 for use in draining fluid from, or supplying medication to, a wound in a patient includes a drain 110 preconnected to a flexible outflow tube 120 via a means 130 connecting the outflow tube 120 to the drain 110. The drain 110 and a small part of the flexible outflow tube 120 are placed in the patient's body 140 with the drain 110 in fluid communication with the wound 150. Preferably, the flexible outflow tube 120 is connected to a sealed, sterilized suction device 190 for drawing fluid through the wound drain catheter 100. In addition, it is also preferable that the outflow tube 120 exit the patient's body 140 through an aperture 141 formed in healthy tissue adjacent to the wound 150. Further, the outflow tube 120 should have a smooth exterior to permit the surface tissue surrounding the aperture 141 to seal against the exterior of the tube 120, and thus, prevent air from passing therebetween. Thus, since the drain 110 is open only to the sterile suction device, and not to the atmosphere, the risk of infection is reduced. Preferably, the outflow tube 120 and the drain 110 are connected end-to-end in an abutting relationship. The means conforming (connecting means) 130 the outflow tube 120 to the drain 110 may comprise a collar.

Drain 110 is positioned in wound 150 by first inserting trocar 170 into wound 150 at a first location 141 and then exiting the trocar 170 from the wound at a second location 142. After wound drain catheter 100 is in place in wound 150, drain 110 is cut near trocar 170 (at P), trocar 170 is discarded, and convoluted sealer/retainer 180 is firmly attached to first location 141 to seal against the exterior of the outflow tube 120 and wound 150, and thus prevent air from passing therebetween. Preferably, outflow tube 120 exiting patient's body 140 is manufactured preconnected to convoluted sealer/retainer 180. The outflow tubing has two "depth marks", 121 and 122, which indicate the recommended range of the depth location for drain catheter 100 inside of the wound 150. The flexible corrugated tubular sealing means 180 is preconnected in a longitudinal direction of the outflow tube 120 on the range closer to the distal depth mark, 121, but the position can be adjusted to depth mark 122 if necessary by sliding outflow tube 120 through the flexible corrugated tubular sealing means 180. Thus, since the wound drain catheter 100, including flexible corrugated tubular sealing means 180 and the suction device 190, are manufactured preconnected in an air tight sterile system, the risk of infection is minimized.

The wound drain catheters 110 of the present invention are preferably made from a silicone elastomer or a bioabsorbable polymer since such materials are biocompatible, soft, and flexible. Preferably, the drain catheter and outflow tubing, in contact with the tissue, has an antifriction coating type. Materials such as PVC are less biocompatible and are more rigid and tend to irritate wounds causing discomfort and inhibiting healing. Materials such as natural rubber are rarely used because of toxicity problems.

Figure 2:
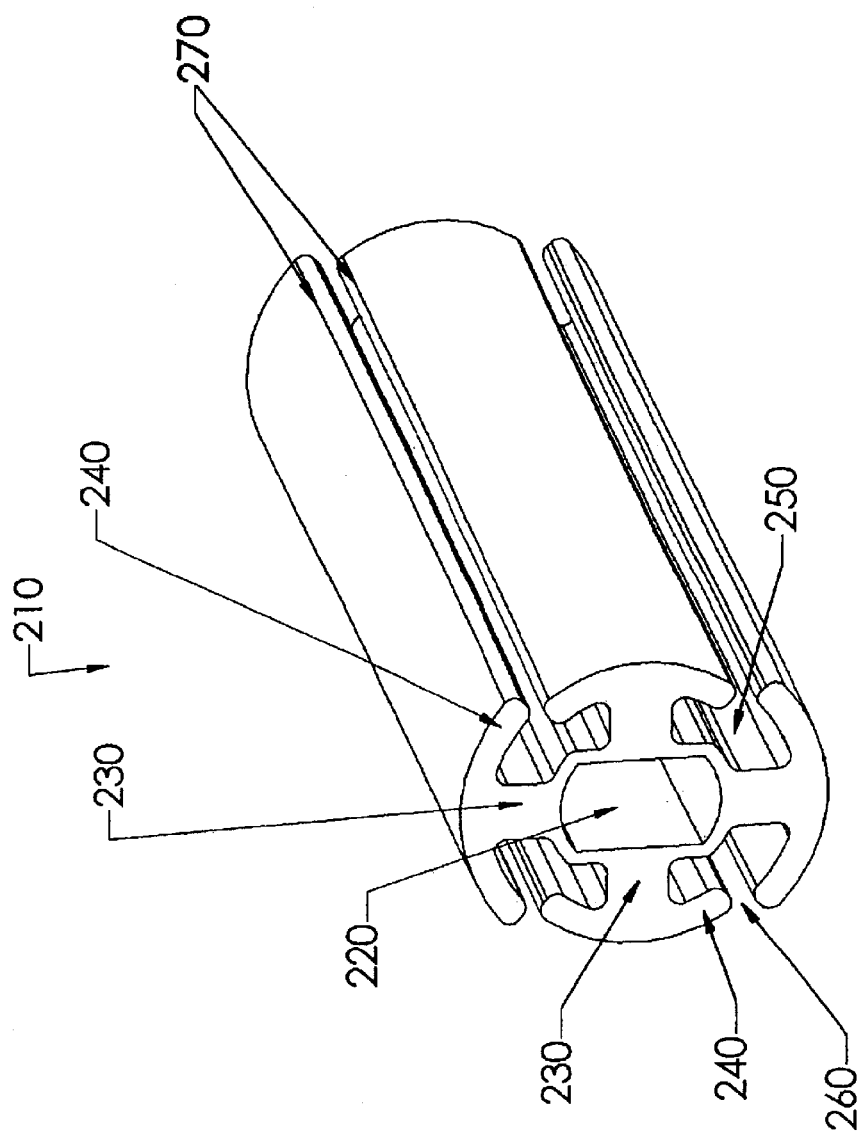
FIG. 2 is a schematic drawing of a first embodiment of the present invention showing a round fluted wound drain catheter with a hollow core portion and four lumens.

FIG. 2 is a schematic drawing of the drain in the wound drain catheter in a preferred embodiment of the present invention. In FIG. 2, the drain is depicted generally as 210 and is constructed in accordance with a preferred embodiment of the present invention. The drain 210 comprises a hollow core portion 220 having a longitudinal axis. Plural strut portions 230 extend outwardly from the hollow core 220. The plural struts 230 are closed to the hollow core portion 220. Plural overhang portions 240 are connected to the outward ends of the strut portions 230, respectively. The overhang portions 240 cooperate with the strut portions 230 to form plural longitudinal lumens 250. The overhang portions 240 cooperate with each other to form, on the outer surface of the drain, the segments of a segmented, closed curve, the gaps 260 between the segments providing plural longitudinal grooves 270 for fluid communication between the wound 150 and the plural lumens 250. The grooves 270 are sized to inhibit tissue from growing therein and debris from passing therethrough. Optionally, the plural strut portions 230 may combine with respective plural overhang portions 240 to form plural T-shaped members which may or may not be the same size.

The hollow core portion 220 may be any shape including round, oval, 3-sided, square, rectangular, 5-sided, and the like, depending upon the ultimate use of the wound drain catheter. The hollow core 220 may be filled with biocompatible liquids or gases or combinations of both. The hollow core 220 may also be filled with one or more biocompatible springs. The drain 210 may have a plurality of strut portions 230 such as two, three, four, or more strut portions 230, extending from the hollow core portion 220. The plural strut portions 230 may or may not project radially from the hollow core portion 220 at equal or unequal angles relative to each other. The drain 210 may be uniform in cross-section throughout its length. The longitudinal grooves 270 may be parallel to the longitudinal axis. The drain 210 may be radially symmetrical. The radially symmetrical drain 210 may have corresponding portions of the drain on each of equiangular, plural radii extending from the central axis, and the corresponding portions are equidistant from the central axis. The drain may have diametrical symmetry. The closed curve may be a circle or may be an oval. Preferably, the closed curve is an oval.

Figure 3:
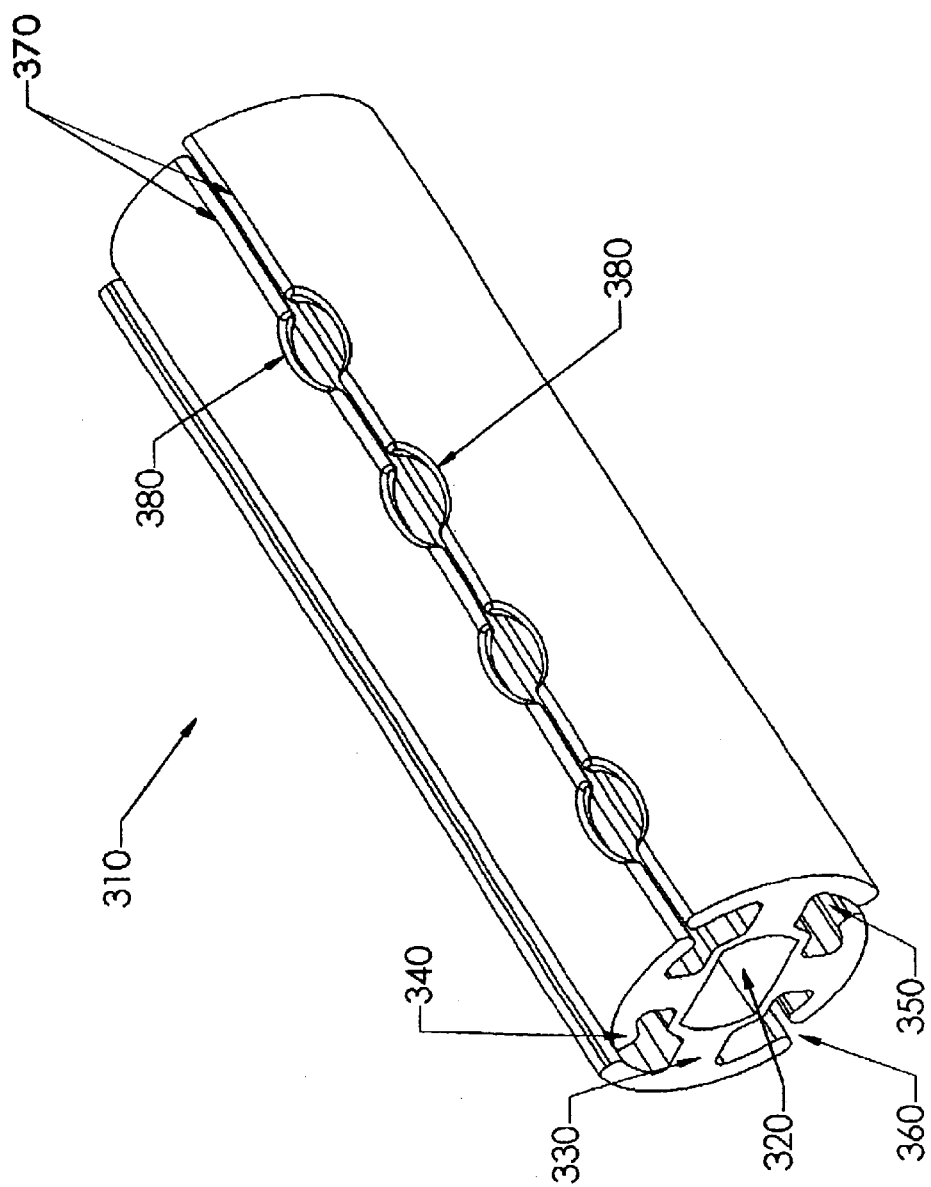
FIG. 3 is another schematic drawing of the drain catheter shown in FIG. 2 illustrating spaced apertures.

FIG. 3 is another schematic drawing of the drain catheter shown in FIG. 2 illustrating spaced apertures. In FIG. 3, the drain is depicted generally as 310 and is constructed in accordance with a preferred embodiment of the present invention. The drain 310 comprises a hollow core portion 320 having a longitudinal axis. Plural strut portions 330 extend outwardly from the hollow core 320 and plural overhang portions 340 are connected to the outward ends of the strut portions 330, respectively. The overhang portions 340 cooperate with the strut portions 330 to form plural longitudinal lumens 350. The overhang portions 340 cooperate with each other to form, on the outer surface of the drain, a segmented, closed curve, the gaps 360 between the segments providing plural longitudinal grooves 370 for fluid communication between the wound and the plural lumens 350. Plural overhang portions 340 have plural spaced apertures 380 on the outward ends thereof. The plural spaced apertures 380 may or may not be evenly spaced. The spaced apertures 380 provide for fluid communication between the wound and the plural lumens 350.

Figure 4:
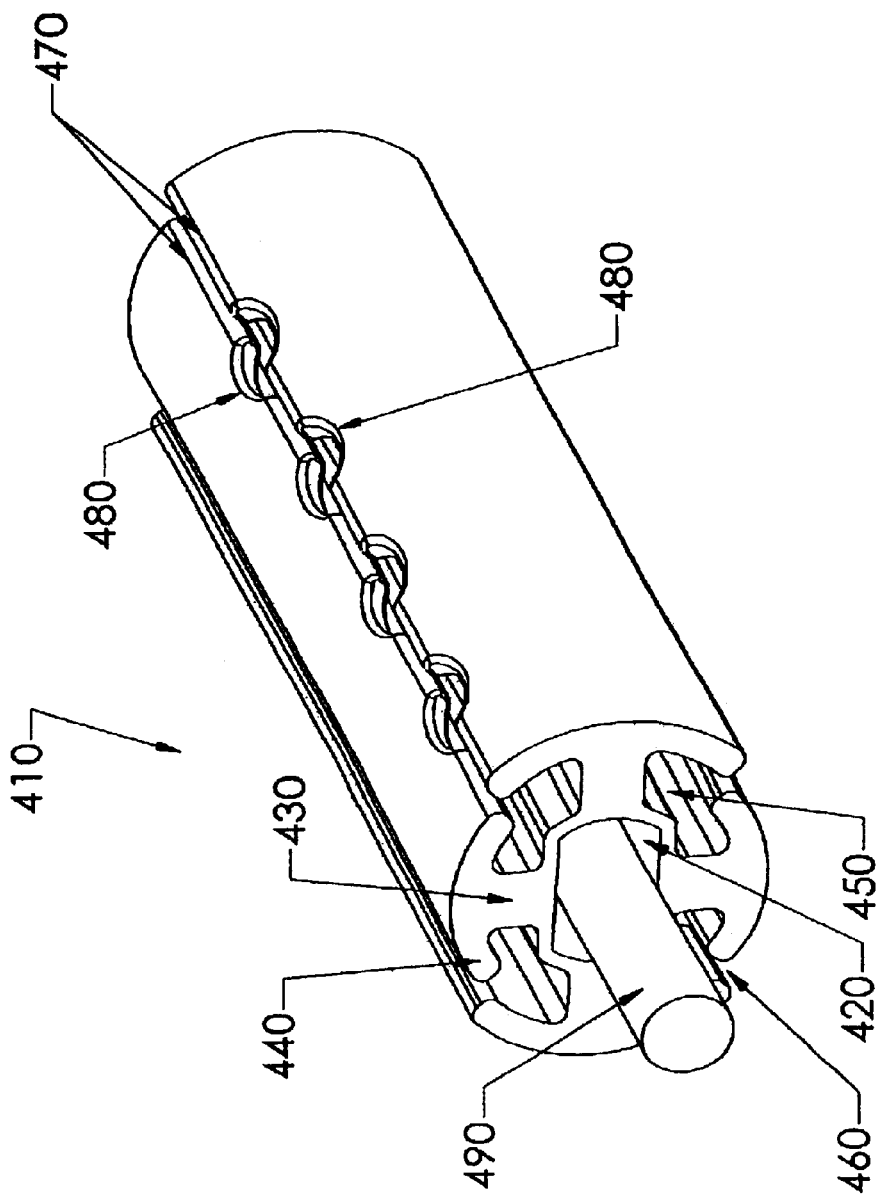
FIG. 4 is another schematic drawing of the drain catheter shown in FIG. 2 illustrating spaced apertures and a constraint suture.

FIG. 4 is another schematic drawing of the drain catheter shown in FIG. 2 illustrating spaced apertures and a constraint suture. In FIG. 4, the drain is depicted generally as 410 and is constructed in accordance with a preferred embodiment of the present invention. The drain 410 comprises a hollow core portion 420 having a longitudinal axis. Plural strut portions 430 extend outwardly from the hollow core 420 and plural overhang portions 440 are connected to the outward ends of the strut portions 430, respectively. The overhang portions 440 cooperate with the strut portions 430 to form plural longitudinal lumens 450. The overhang portions 440 cooperate with each other to form, on the outer surface of the drain, a segmented, closed curve, the gaps 460 between the segments providing plural longitudinal grooves 470 for fluid communication between the wound and the plural lumens 450. Plural overhang portions 440 have plural spaced apertures 480 on the outward ends thereof. One or more constraint sutures or wires 490 are present inside the hollow core portion 420. A first end of the constraint suture 490 may be attached to a proximal end of the drain 410 and a second end of the constraint suture 490 may be attached to a distal end of the drain 410 or to the flexible outflow tube. The constraint suture 490 provides additional cross-sectional strength and prevents breakage of the drain 410 during removal. The use of constraint or reinforcing sutures 490 also permits the use of a smaller diameter and more pliable drain system 410 with thinner walls without decreasing the strength of the drain catheter.

Figure 5:
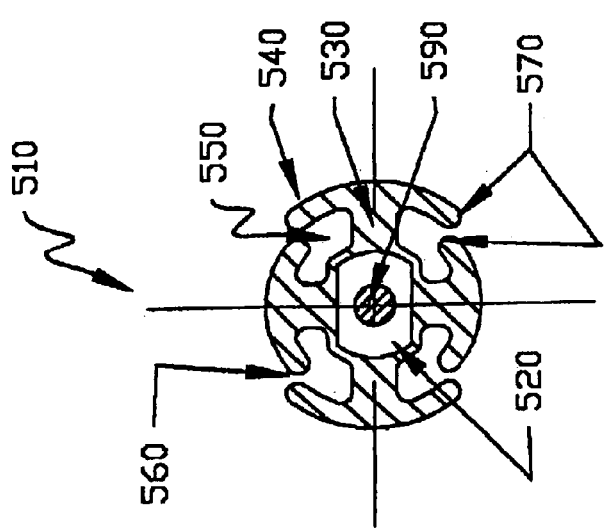
FIG. 5 is a lateral cross-sectional view of the drain catheter shown in FIG. 4.

FIG. 5 is a lateral cross-sectional view of the drain catheter shown in FIG. 4. In FIG. 5, the drain is depicted generally as 510 and is constructed in accordance with a preferred embodiment of the present invention. The drain 510 comprises a hollow core portion 520 having a longitudinal axis. Plural strut portions 530 extend outwardly from the hollow core 520 and plural overhang portions 540 are connected to the outward ends of the strut portions 530, respectively. The overhang portions 540 cooperate with the strut portions 530 to form plural longitudinal lumens 550. The overhang portions 540 cooperate with each other to form, on the outer surface of the drain, a segmented, closed curve, the gaps 560 between the segments providing plural longitudinal grooves 570 for fluid communication between the wound and the plural lumens 550. Plural overhang portions 540 have plural spaced apertures (not shown) on the outward ends thereof. One or more constraint sutures 590 are present inside the hollow core portion.

Figure 6:
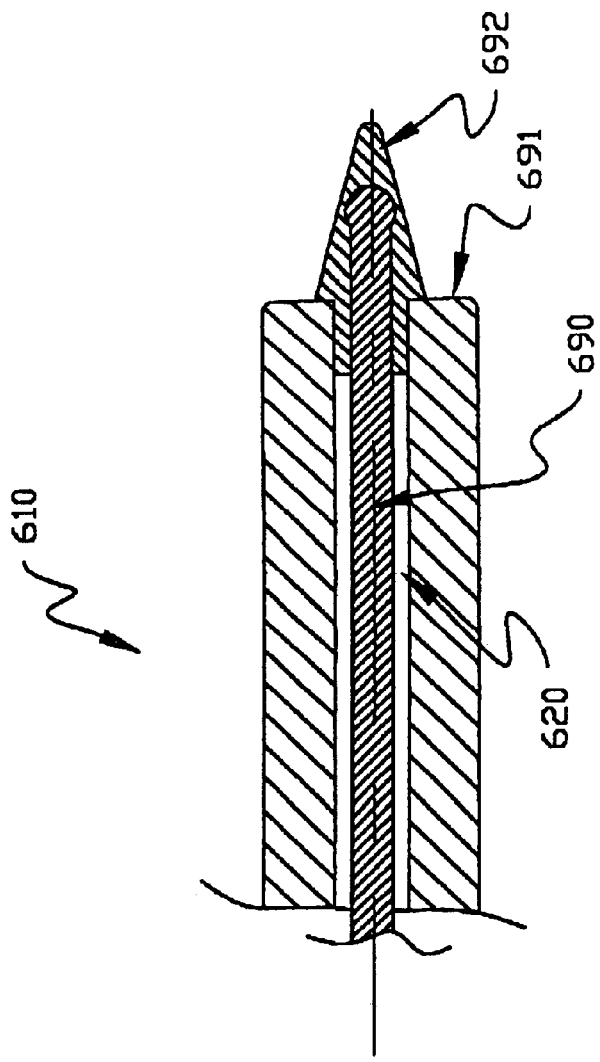
FIG. 6 is a longitudinal cross-sectional view of the drain catheter shown in FIG. 4.

FIG. 6 is a longitudinal cross-sectional view of the drain catheter shown in FIG. 4. In FIG. 6, the drain is depicted generally as 610 and is constructed in accordance with a preferred embodiment of the present invention. A constraint suture 690 is present inside the hollow core portion 620. A first end of the constraint suture 690 is attached to a proximal end of the drain 691 via a plug 692. A second end of the constraint suture 690 is attached to a distal end of the drain or to the flexible outflow tube (not shown).

FIG. 7 is a lateral cross-sectional view of the drain catheter shown in FIG. 4 in relationship to a wound 150. In FIG. 7, the drain is depicted generally as 710 and is constructed in accordance with a preferred embodiment of the present invention. The drain 710 comprises a rectangular hollow core portion 720 with a constraint suture 790 present inside the hollow core portion 720. Plural overhang portions 740 are connected to the outward ends of the strut portions 730, respectively, to form large T-shaped members 741 and small T-shaped members 742. Large T-shaped members 741 are connected to a relatively small cross sectional area of rectangular hollow core portion 720 and small T-shaped members 742 are connected to a relatively large cross sectional area of rectangular hollow core portion 720. The shape of the drain 710 in relationship to the wound 150 is shown when the pressure in the rectangular hollow core 720 is one atmosphere.

FIG. 8 is a lateral cross-sectional view of the drain catheter shown in FIG. 7 in relationship to a wound 150. In FIG. 8, the drain is depicted generally as 810 and is constructed in accordance with a preferred embodiment of the present invention. The shape of the drain catheter 810 in relationship to the wound 150 is shown when the pressure in the hollow core 820 is increased above one atmosphere. Because large T-shaped members 841 are connected to a relatively small cross sectional area of rectangular hollow core portion 820 and small T-shaped members 842 are connected to a relatively large cross sectional area of rectangular hollow core portion 820, small T-shaped members 842 expand to meet large T-shaped members 841 as the pressure in the hollow core 820 is increased above one atmosphere.

FIG. 9 is a lateral cross-sectional view of the drain catheter shown in FIG. 7 in relationship to a wound 150. In FIG. 9, the drain is depicted generally as 910 and is constructed in accordance with a preferred embodiment of the present invention. The shape of the drain catheter 910 in relationship to the wound 150 is shown when the pressure in the hollow core is at maximum pressure. Because large T-shaped members 941 are connected to a relatively small cross sectional area of rectangular hollow core portion 920 and small T-shaped members 942 are connected to a relatively large cross sectional area of rectangular hollow core portion 920, small T-shaped members 942 expand past large T-shaped members 941 to form reversed gaps as the pressure in the hollow core 920 is increased above one atmosphere.

This ability to change the size of the gaps in the wound drain catheter of the present invention helps to keep the drain efficient, relieves the gripping force on the tissue, and makes the wound drain catheter easier to remove from the patient, and reduces the risk of damage to the tissues surrounding the wound. The hollow tube portion may be inflated or deflated to accommodate the draining process. This is especially important during removal of the wound drain catheter. Deflating the wound drain catheter prior to removing it with a strong pulling force counters the tendency of the wound drain catheter to decrease in diameter when pulled and thereby minimizes pinching and the subsequent trapping of any tissue that has grown into the drain during drain removal. The hollow core of the wound drain catheter may be filled with biocompatible liquids or gases or combinations of both. The hollow core of the wound drain catheter may also be filled with one or more biocompatible springs. The different levels of pressure in the hollow core helps control the effectiveness of the drain process and eliminates tissue trauma during removal of the drain catheter from the patient.

Figure 10:
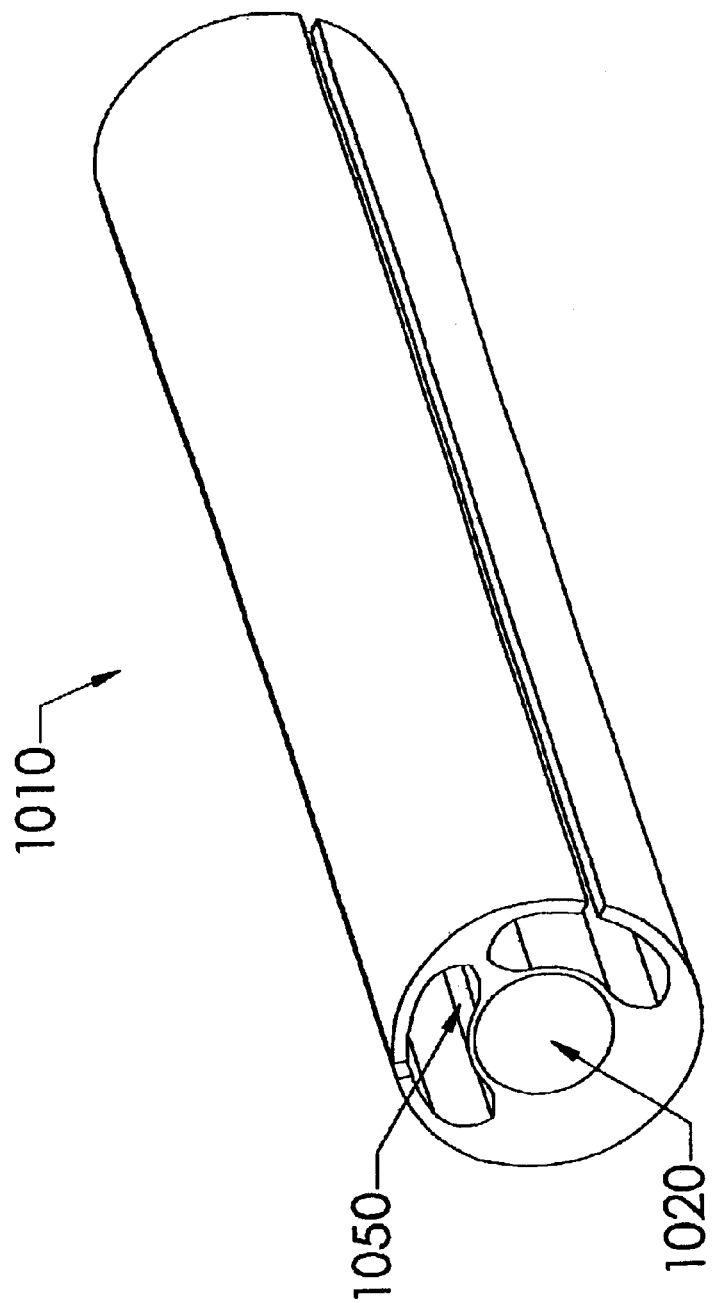
FIG. 10 is a schematic drawing of a round fluted wound drain catheter with a hollow core portion and two lumens.

FIG. 10 is a schematic drawing of a round fluted wound drain catheter 1010 with a hollow core portion 1020 and two lumens 1050.

Figure 11:
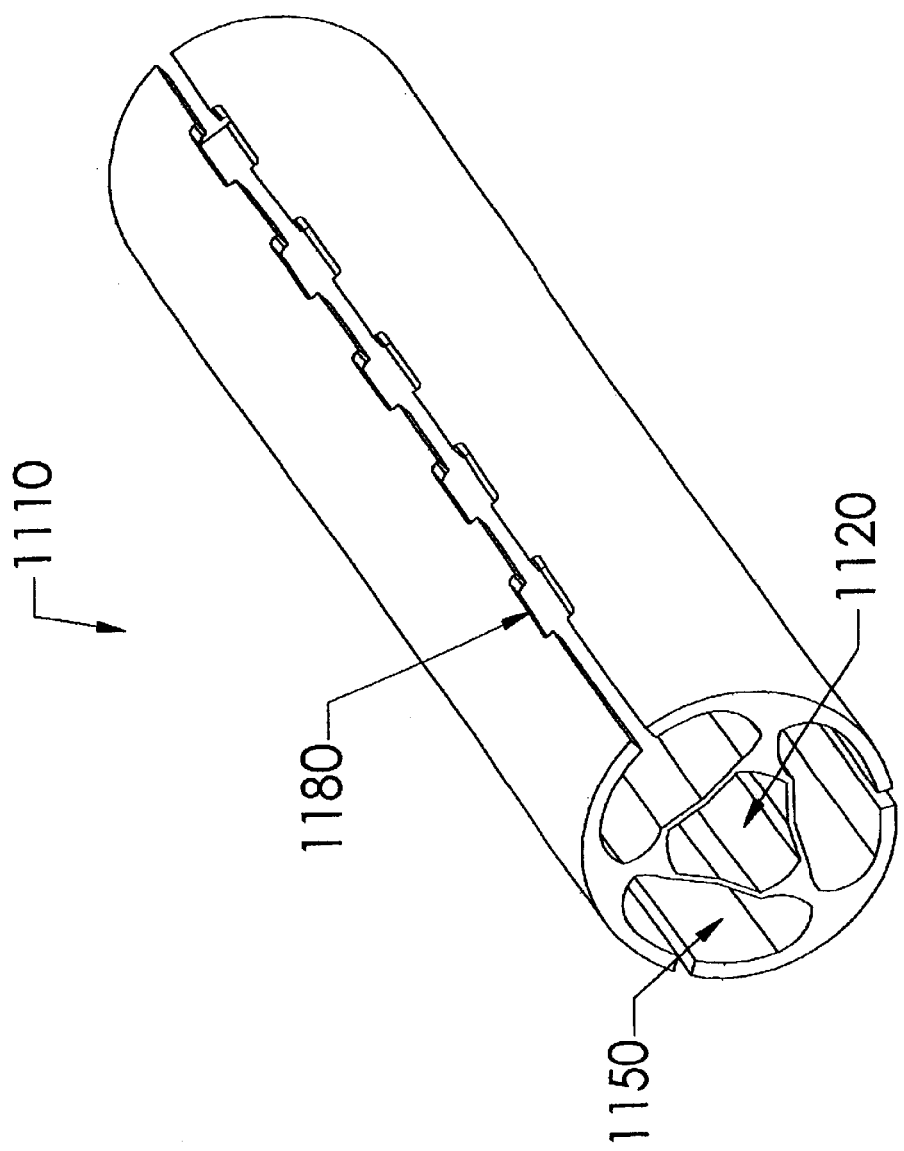
FIG. 11 is a schematic drawing of a round fluted wound drain catheter with a hollow core portion, three lumens, and spaced apertures.

FIG. 11 is a schematic drawing of a round fluted wound drain catheter 1110 with a hollow core portion 1120, three lumens 1150, and spaced apertures 1180.

The drain catheter may further incorporate a radiopaque material so that the drain catheter is opaque to various forms of radiation, such as X-rays. In this way, the location of the drain catheter may be determined in the body of a patient.

Several techniques may be employed to insert a wound drain catheter into a patient. For example, a surgeon may simply place the drain portion and a small part of the outflow tube portion in the wound, close the incision, and suture around the outflow tube portion. This technique is somewhat unsatisfactory since it is difficult to completely seal the area around the outflow tube by suturing, and thus, the wound may become infected. A more satisfactory technique is to pass a trocar, preattached to the end of the outflow tube, through healthy tissue by entering the patient at a point within the wound and exiting at a point adjacent to the wound. The surgeon may then pull the outflow tube portion through the tissue with the trocar until the catheter is properly positioned, with the drain in the wound. Since the outflow tube exits the body at a point adjacent the wound, the wound can be completely closed by suturing thereby reducing the risk of infection.

In another embodiment, the present invention pertains to a method for draining fluid from, or supplying medication to, a wound in a patient comprising:
(1) providing a drain catheter having a flexible outflow tube;
(2) placing the drain catheter and the flexible outflow tube in the wound of a patient;
(3) closing the wound to seal the wound from the atmosphere;
(4) connecting the flexible outflow tube to a reservoir; and
(5) removing the drain catheter from the wound by applying a tensile force;
wherein the drain catheter comprises:

(A) a drain comprising:
   (a) a hollow core having a longitudinal axis;
   (b) plural struts extending outwardly from the hollow core and being closed to the hollow core; and
   (c) plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough;
(B) a flexible outflow tube having a smooth exterior for sealing to surface tissue at the point of exit from the body of a patient; and
(C) means conforming to the segmented, closed curve for connecting the drain to the flexible outflow tube.

In yet another embodiment, the present invention pertains to a wound drain catheter system for draining fluid from, or supplying medication to, a wound in a patient comprising:
(A) a trocar having:
   (a) a blade portion on a distal end; and
   (b) a connector portion on a proximal end, the connector portion being a hollow core lying on a longitudinal axis;
(B) a drain having:
   (a) a first connector portion on a distal end, the first connector portion being a protrude lying on a longitudinal axis; and
   (b) a second connector portion on a proximal end;
(C) a flexible outflow tube having:
   (a) a proximal end and a distal end; and
   (b) a smooth exterior for sealing to surface tissue at the point of exit from the body of a patient; and
(D) means for connecting the second connector portion of the drain to the distal end of the flexible outflow tube;
wherein the protrude of the first connector portion of the drain engages the interior of the hollow core of the connector portion of the trocar.

Figure 12:
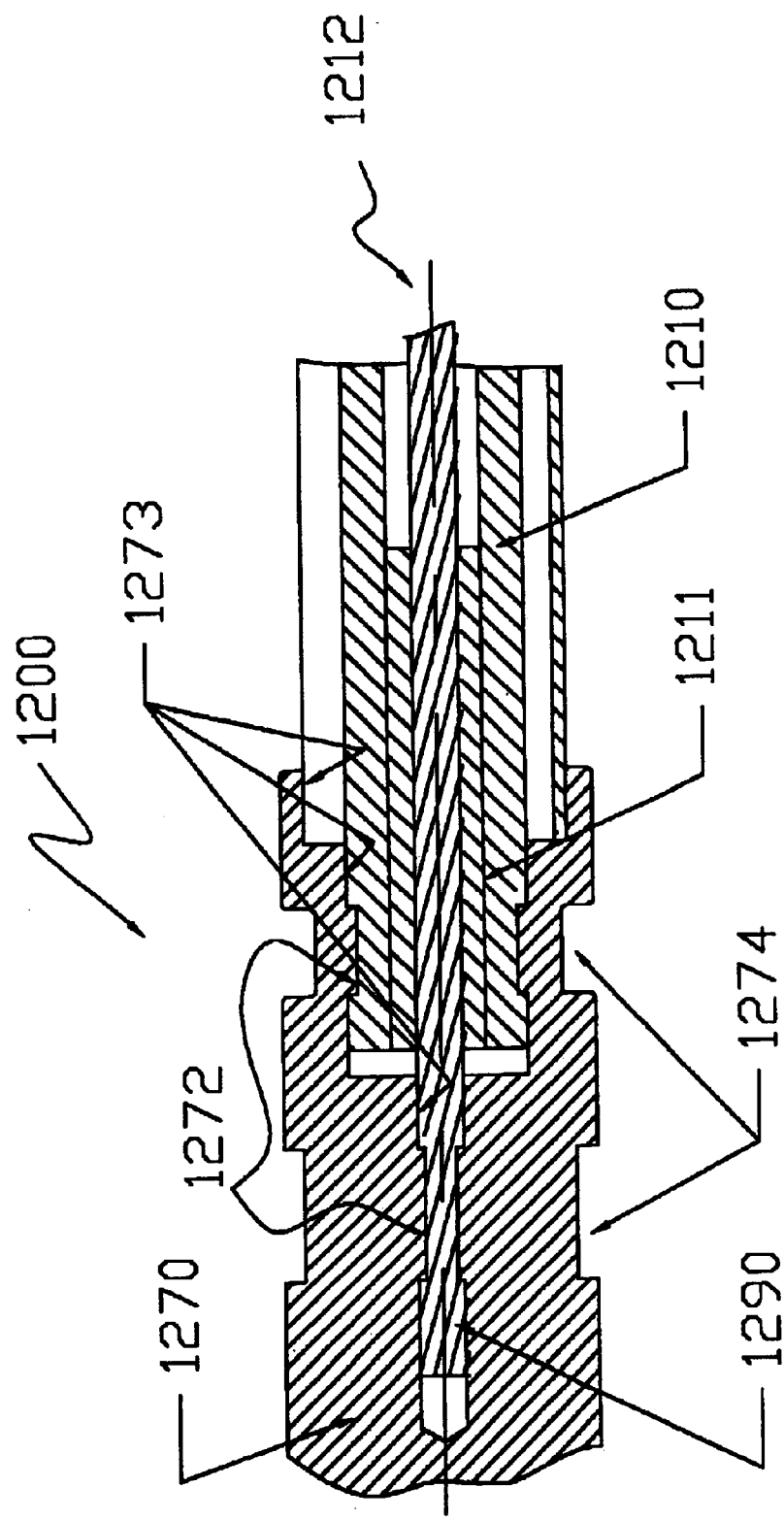
FIG. 12 is a longitudinal cross-sectional view of the attachment of the trocar to a distal end of the wound drain catheter system for draining fluid from, or supplying medication to, a wound in a patient in a preferred embodiment of the present invention.

FIG. 12 is a longitudinal cross-sectional view of the wound drain catheter system for draining fluid from, or supplying medication to, a wound in a patient in a preferred embodiment of the present invention. The drain and part of the outflow tube are placed in a closed, deep wound in the body of a patient. In FIG. 12, the wound drain catheter system is depicted generally as 1200 and is constructed in accordance with a preferred embodiment of the present invention. Trocar 1270 has a blade portion (171, FIG. 1) on a distal end and a connector portion 1272 on a proximal end. The connector portion 1272 is a hollow core lying on a longitudinal axis of the trocar 1270. A drain 1210 has a first connector portion 1211 on a distal end. The first connector portion 1211 is a protrude lying on a longitudinal axis. A second connector portion 1212 is included on a proximal end of the drain 1210. A flexible outflow tube (120, FIG. 1) has a proximal end (120*p*, FIG. 1) and a distal end (120*d*, FIG. 1) and a smooth exterior for sealing to surface tissue at the point of exit from the body of a patient. A means (130, FIG. 1) is included for connecting the second connector portion of the drain 1212 to the distal end of the flexible outflow tube 120*d*. The protrude 1211 of the first connector portion of the drain engages the interior of the hollow core of the connector portion 1272 of the trocar.

The connector portion of the trocar 1272 may be swagged 1272/1274 to grippingly engage the protrude 1211 in the first connector portion of the drain. The protrude 1211 in the first connector portion of the drain may have annular ridges to grippingly engage the interior of the hollow core of the connector portion 1272 of the trocar. The annular ridges may be made by a swaging process after insertion of the drain catheter into step holes 1273 of trocar 1270 (before insertion of the drain catheter into step holes 1273 of trocar 1270 there are no ridges). The drain may further comprise a constraint suture or wire 1290.

Preferably, the trocar, drain, flexible outflow tube, and means for connecting the drain to the flexible outflow tube are a unitary sterile system. The wound drain catheter system may further comprise a suction device (190, FIG. 1) connected to the proximal end of the flexible outflow tube 120*p*. Preferably, the trocar, drain, flexible outflow tube, means for connecting the drain to the flexible outflow tube, and the suction device are a unitary sterile system.

In a preferred embodiment, the drain is of the type fully described in FIG. 2. Specifically, the drain comprises (a) a hollow core having a longitudinal axis; (b) plural struts extending outwardly from the hollow core and being closed to the hollow core; and (c) plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough. Preferably, at least one lumen in the drain is closed from the suction device and supplies medication to, and balances pressure in, the wound.

Figure 13:
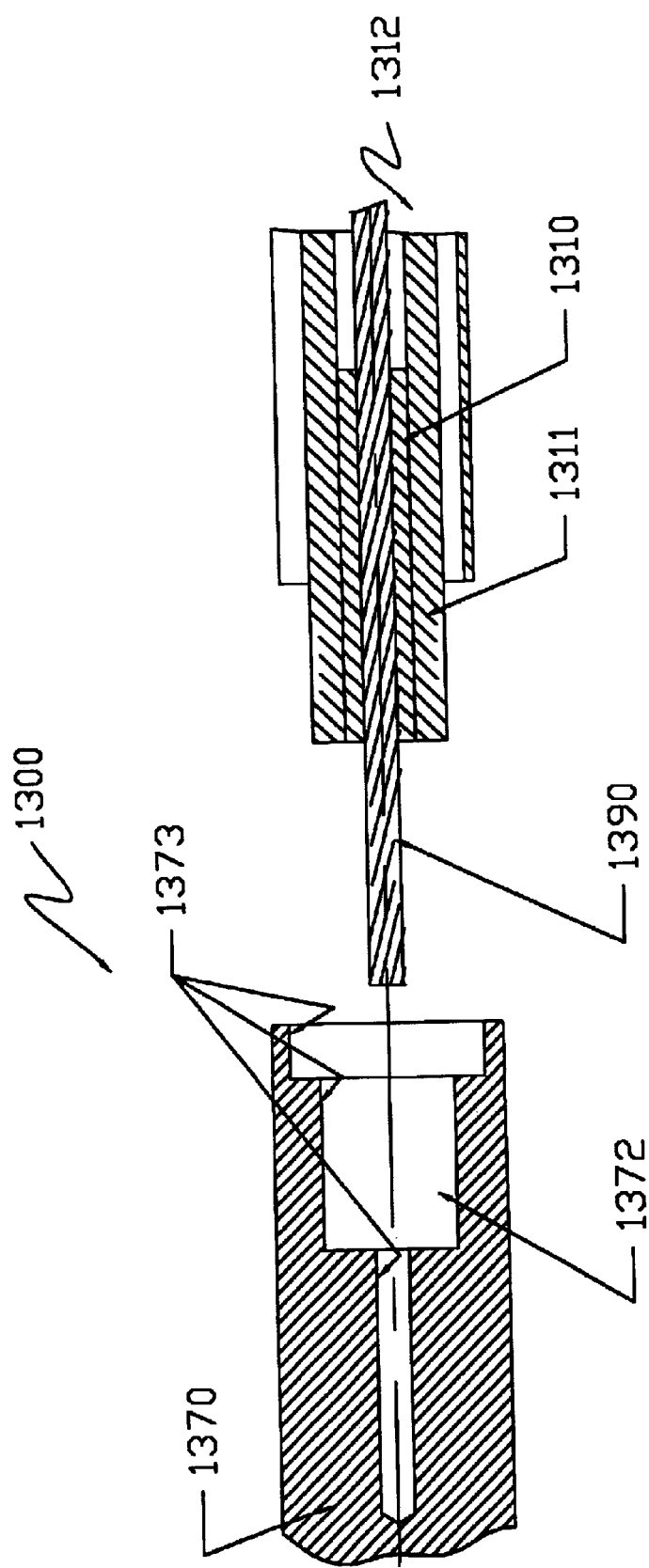
FIG. 13 is an expanded view of the preattached wound drain catheter system shown in FIG. 12.

Preferably, the protrude 1211 in the distal end of the wound drain catheter 1210 is preconnected to the proximal end of the trocar 1372 (FIG. 13). The distal end of the wound drain catheter with protrude 1211 is inserted in the step hole 1273 of the trocar 1270. After insertion of the distal end of the catheter 1211 to the proximal end of the trocar 1372 (FIG. 13), the trocar 1270 is attached to the drain 1210 by swaging or by any other known attaching methods in the art. This sterile wound drain system with preconnected trocar to the distal end of the catheter and with preconnected vacuum device to the proximal end of catheter allows decrease time in the operating room and minimizes the chance for infection.

FIG. 13 is an expanded view of the preattached wound drain catheter system shown in FIG. 12. In FIG. 13, the wound drain catheter system is depicted generally as 1300 and is constructed in accordance with a preferred embodiment of the present invention. Trocar 1370 has a blade portion (171, FIG. 1) on a distal end and a connector portion 1372 on a proximal end. The connector portion 1372 is a hollow core lying on a longitudinal axis of the trocar 1370. A drain 1310 has a first connector portion 1311 on a distal end. The first connector portion 1311 is a protrude lying on a longitudinal axis. A second connector portion 1312 is included on a proximal end of the drain 1310. A flexible outflow tube (120, FIG. 1) has a proximal end (120*p*, FIG. 1) and a distal end (120*d*, FIG. 1). A means (130, FIG. 1) is included for connecting the second connector portion of the drain 1312 to the distal end of the flexible outflow tube 120*d*. The protrude 1311 of the first connector portion of the drain engages the interior of the hollow core of the connector portion 1372 of the trocar. The drain may further comprise a constraint suture or wire 1390.

In yet another embodiment, the present invention pertains to a wound drain catheter system for draining fluid from, or supplying medication to, a wound in a patient comprising:

(A) a trocar having:
  (a) a blade portion on a distal end; and
  (b) a connector portion on a proximal end, the connector portion being a hollow core lying on a longitudinal axis;
(B) a bioabsorbable transitional part having:
  (a) a first connector portion on a distal end, the first connector portion being a protrude lying on a longitudinal axis;
  (b) a connector portion on a proximal end, the connector portion being a hollow core lying on a longitudinal axis; and
  (c) a stop portion being substantially perpendicular to the longitudinal axis of the bioabsorbable transitional part;
(C) a drain having:
  (a) a first connector portion on a distal end, the first connector portion being a protrude lying on a longitudinal axis; and
  (b) a second connector portion on a proximal end;
(D) a flexible outflow tube having:
  (a) a proximal end and a distal end; and
  (b) a smooth exterior for sealing to surface tissue at the point of exit from the body of a patient; and
(E) means for connecting the second connector portion of the drain to the distal end of the flexible outflow tube;

wherein the protrude of the first connector portion of the drain engages the interior of the hollow core of the connector portion of the bioabsorbable transitional part and the protrude of the bioabsorbable transitional part grippingly engages the interior of the hollow core of the connector portion of the trocar.

Figure 14:
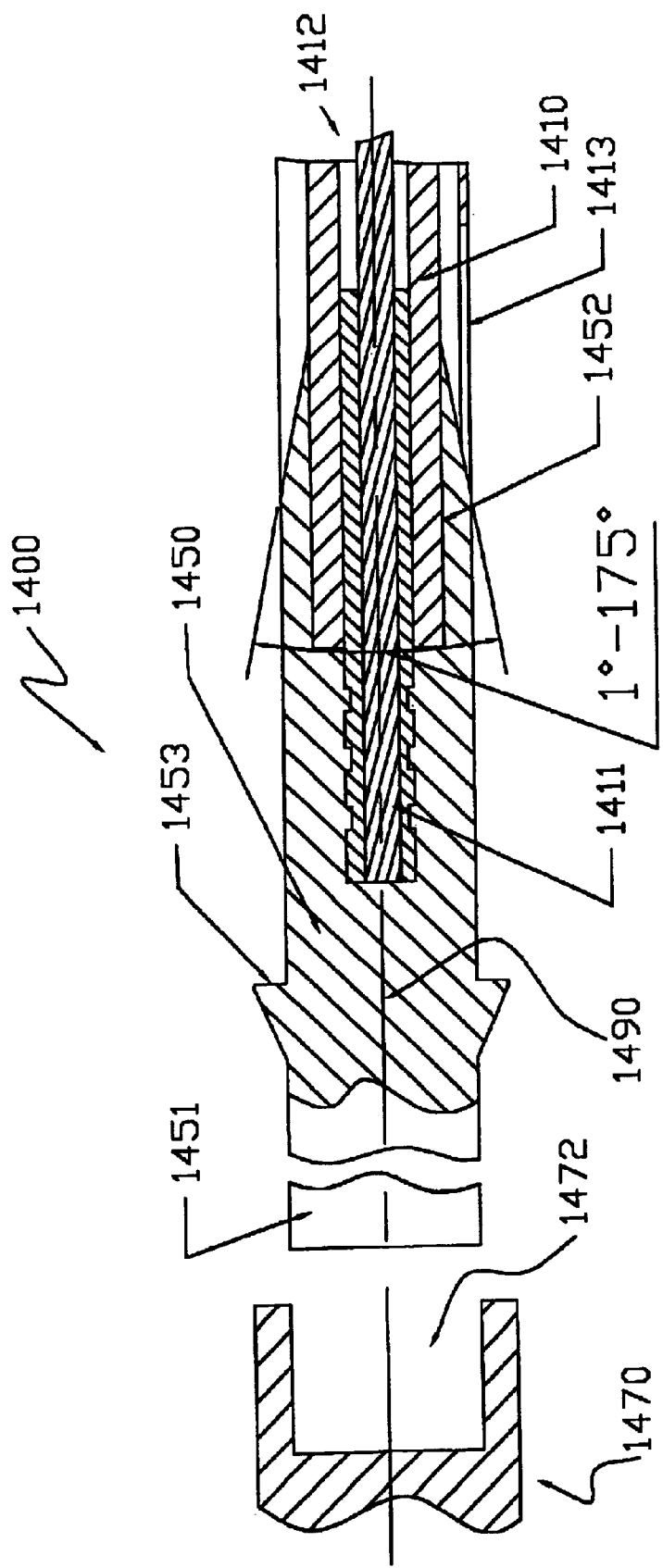
FIG. 14 is a longitudinal cross-sectional view of the wound drain catheter system for draining fluid from, or supplying medication to, a wound in a patient in a preferred embodiment of the present invention.

FIG. 14 is a longitudinal cross-sectional view of the wound drain catheter system for draining fluid from, or supplying medication to, a wound in a patient in a preferred embodiment of the present invention. The drain and part of the outflow tube are placed in a closed, deep wound in the body of a patient. In FIG. 14, the wound drain catheter system is depicted generally as 1400 and is constructed in accordance with a preferred embodiment of the present invention. Trocar 1470 has a blade portion (171, FIG. 1) on a distal end and a connector portion 1472 on a proximal end. The connector portion 1472 is a hollow core lying on a longitudinal axis of the trocar 1470. A bioabsorbable transitional part 1450 has a first connector portion 1451 on a distal end. The first connector portion 1451 is a protrude lying on a longitudinal axis of the bioabsorbable transitional part 1450. A connector portion 1452 is included on a proximal end. The connector portion 1452 is a hollow core lying on a longitudinal axis of the bioabsorbable transitional part 1450. A stop portion 1453 is substantially perpendicular to the longitudinal axis of the bioabsorbable transitional part 1450. A drain 1410 has a first connector portion 1411 on a distal end. The first connector portion 1411 is a protrude lying on a longitudinal axis of the drain 1410. A second connector portion 1412 is included on a proximal end. A flexible outflow tube (120, FIG. 1) has a proximal end 120*p* and a distal end 120*d*. The flexible outflow tube 120 has a smooth exterior for sealing to surface tissue at the point of exit from the body of a patient. A means (130, FIG. 1) is included for connecting the second connector portion 1412 of the drain to the distal end 120*d* of the flexible outflow tube. The protrude 1411 of the first connector portion of the drain 1410 grippingly engages the interior of the hollow core of the connector portion 1452 of the bioabsorbable transitional part 1450 and the protrude 1451 of the bioabsorbable transitional part 1450 grippingly engages the interior of the hollow core of the connector portion 1472 of the trocar 1470.

Preferably, the connector portion 1452 on the proximal end of the bioabsorbable transitional part is beveled.

Preferably, the connector portion on the proximal end of the bioabsorbable transitional part is beveled at an angle from about 1° to about 175°, more preferably from about 5° to about 150°, and most preferably from about 10° to about 100°. Preferably, the drain further comprises a constraint suture or wire 1490.

Preferably, the trocar, bioabsorbable transitional part, drain, flexible outflow tube, and means for connecting the drain to the flexible outflow tube are a unitary sterile system. The wound drain catheter system may further comprise a suction device (190, FIG. 1) connected to the proximal end of the flexible outflow tube 120p. Preferably, the trocar, bioabsorbable transitional part, drain, flexible outflow tube, means for connecting the drain to the flexible outflow tube, and the suction device are a unitary sterile system.

In a preferred embodiment, the drain is of the type fully described in FIG. 2. Specifically, the drain comprises (a) a hollow core having a longitudinal axis; (b) plural struts extending outwardly from the hollow core and being closed to the hollow core; and (c) plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough. Preferably, at least one lumen in the drain is closed from the suction device and supplies medication to the wound.

A cylindrical portion of the bioabsorbable part 1450 will protrude through the body and be sutured to skin and covered by dressing. The excess of bio-absorbable part may be cut off and covered by dressing when the patient no longer requires a drain system. This kind of design will decrease infection under the skin, simplify the suturing process and can be used with any wound drain systems. The distal part of the drain 1410 has openings 1413 which help decrease resistance of sliding out trapping tissue. This sterile wound drain system with preconnected trocar to the distal end of the catheter and with preconnected vacuum device to the proximal end of catheter allows decreased time in the operating room and minimizes infection.

Figure 15:
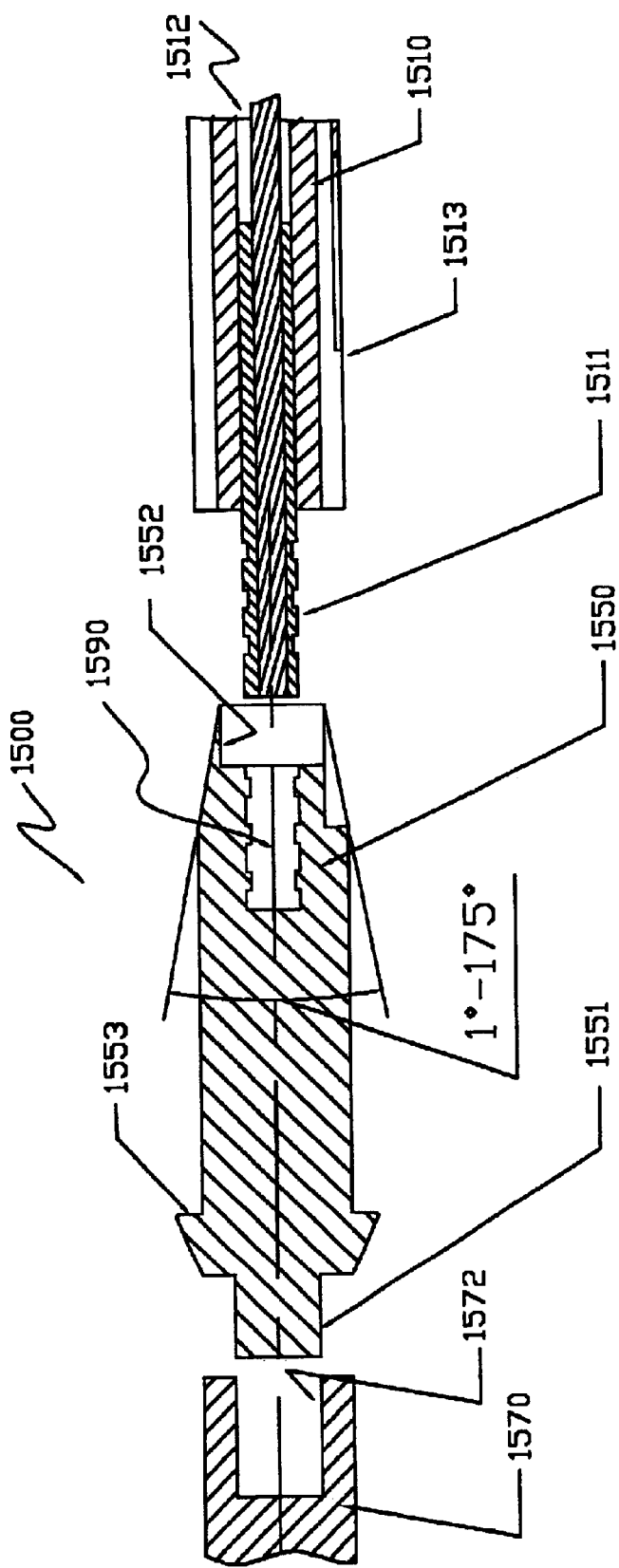
FIG. 15 is an expanded view of the wound drain catheter system shown in FIG. 14.

FIG. 15 is an expanded view of the wound drain catheter system shown in FIG. 14. In FIG. 15, the wound drain catheter system is depicted generally as 1500 and is constructed in accordance with a preferred embodiment of the present invention. Trocar 1570 has a blade portion (171, FIG. 1) on a distal end and a connector portion 1572 on a proximal end. The connector portion 1572 is a hollow core lying on a longitudinal axis of the trocar 1570. A bioabsorbable transitional part 1550 has a first connector portion 1551 on a distal end. The first connector portion 1551 is a protrude lying on a longitudinal axis of the bioabsorbable transitional part 1550. A connector portion 1552 is included on a proximal end. The connector portion 1552 is a hollow core lying on a longitudinal axis of the bioabsorbable transitional part 1550. A stop portion 1553 is substantially perpendicular to the longitudinal axis of the bioabsorbable transitional part 1550. A drain 1510 has a first connector portion 1511 on a distal end. The first connector portion 1511 is a protrude lying on a longitudinal axis of the drain 1510. A second connector portion 1512 is included on a proximal end. A flexible outflow tube (120, FIG. 1) has a proximal end 120p and a distal end 120d. The flexible outflow tube 120 has a smooth exterior for sealing to surface tissue at the point of exit from the body of a patient. A means (130, FIG. 1) is included for connecting the second connector portion 1512 of the drain to the distal end 120d of the flexible outflow tube. The protrude 1511 of the first connector portion of the drain 1510 grippingly engages the interior of the hollow core of the connector portion 1552 of the bioabsorbable transitional part 1550 and the protrude 1551 of the bioabsorbable transitional part 1550 grippingly engages the interior of the hollow core of the connector portion 1572 of the trocar 1570.

The present invention comprises a wound drain catheter for draining fluid from, and supplying medication to, a wound in a patient and a method of implementation which, in comparison with prior art drains has a trocar for placing a wound drainage catheter into the body of a patient, which may be manufactured pre-attached to proximal end of the outflow tubing. An external source of vacuum (suction device) may be manufactured pre-attached to the proximal end of the outflow tubing. This type of manufacturing of wound drain catheter pre-assembly allows the surgeon to have a bacteria free device and a method of insertion and restraint of the wound drain catheter in the desired location of the patient's body.

The invention being thus described, it will be obvious that the same may be varied in many ways. Such variations are not to be regarded as a departure from the spirit and scope of the invention and all such modifications are intended to be included within the scope of the following claims.

What is claimed is:

1. A wound drain catheter system for draining fluid from, or supplying medication to, a wound in a patient comprising:
    (A) a trocar having:
        (a) a blade portion on a distal end; and
        (b) a connector portion on a proximal end, the connector portion being a hollow core lying on a longitudinal axis;
    (B) a drain having:
        (a) a first connector portion on a distal end, the first connector portion being a protrude lying on a longitudinal axis; and
        (b) a second connector portion on a proximal end;
    (C) a flexible outflow tube having:
        (a) a proximal end and a distal end; and
        (b) a smooth exterior for sealing to surface tissue at the point of exit from the body of a patient; and
    (D) means for connecting the second connector portion of the drain to the distal end of the flexible outflow tube;
wherein the protrude of the first connector portion of the drain engages the interior of the hollow core of the connector portion of the trocar.

2. The wound drain catheter system according to claim 1, wherein the connector portion of the trocar is swagged to grippingly engage the protrude in the first connector portion of the drain.

3. The wound drain catheter system according to claim 1, wherein the protrude in the first connector portion of the drain has annular ridges to grippingly engage the interior of the hollow core of the connector portion of the trocar.

4. The wound drain catheter system according to claim 1, the drain further comprises a constraint suture or wire.

5. The wound drain catheter system according to claim 1, wherein the trocar, drain, flexible outflow tube, and means for connecting the drain to the flexible outflow tube are a unitary sterile system.

6. The wound drain catheter system according to claim 1, further comprising a suction device connected to the proximal end of the flexible outflow tube.

7. The wound drain catheter system according to claim 6, wherein the trocar, drain, flexible outflow tube, means for connecting the drain to the flexible outflow tube, and the suction device are a unitary sterile system.

8. The wound drain catheter system according to claim 7, wherein the drain comprises:
   (a) a hollow core having a longitudinal axis;
   (b) plural struts extending outwardly from the hollow core and being closed to the hollow core; and
   (c) plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough.

9. The wound drain catheter system according to claim 8, wherein at least one lumen in the drain is closed from the suction device to supply medication to the wound or to balance pressure inside the patient's body.

10. A wound drain catheter system for draining fluid from, or supplying medication to, a wound in a patient comprising:
   (A) a trocar having:
      (a) a blade portion on a distal end; and
      (b) a connector portion on a proximal end, the connector portion being a hollow core lying on a longitudinal axis;
   (B) a bioabsorbable transitional part having:
      (a) a first connector portion on a distal end, the first connector portion being a protrude lying on a longitudinal axis;
      (b) a connector portion on a proximal end, the connector portion being a hollow core lying on a longitudinal axis; and
      (c) a stop portion being substantially perpendicular to the longitudinal axis of the bioabsorbable transitional part;
   (C) a drain having:
      (a) a first connector portion on a distal end, the first connector portion being a protrude lying on a longitudinal axis; and
      (b) a second connector portion on a proximal end;
   (D) a flexible outflow tube having:
      (a) a proximal end and a distal end; and
      (b) a smooth exterior for sealing to surface tissue at the point of exit from the body of a patient; and
   (E) means for connecting the second connector portion of the drain to the distal end of the flexible outflow tube; wherein the protrude of the first connector portion of the drain engages the interior of the hollow core of the connector portion of the bioabsorbable transitional part and the protrude of the bioabsorbable transitional part grippingly engages the interior of the hollow core of the connector portion of the trocar.

11. The wound drain catheter system according to claim 10, wherein the connector portion on the proximal end of the bioabsorbable transitional part is beveled.

12. The wound drain catheter system according to claim 11, wherein the connector portion on the proximal end of the bioabsorbable transitional part is beveled at an angle from about 1° to about 175°.

13. The wound drain catheter system according to claim 10, the drain further comprises a constraint suture or wire.

14. The wound drain catheter system according to claim 10, wherein the trocar, bioabsorbable transitional part, drain, flexible outflow tube, and means for connecting the drain to the flexible outflow tube are a unitary sterile system.

15. The wound drain catheter system according to claim 10, further comprising a suction device connected to the proximal end of the flexible outflow tube.

16. The wound drain catheter system according to claim 15, wherein the trocar, bioabsorbable transitional part, drain, flexible outflow tube, means for connecting the drain to the flexible outflow tube, and the suction device are a unitary sterile system.

17. The wound drain catheter system according to claim 16, wherein the drain comprises:
   (a) a hollow core having a longitudinal axis;
   (b) plural struts extending outwardly from the hollow core and being closed to the hollow core; and
   (c) plural overhangs connected to the outward ends of the struts, respectively, the overhangs cooperating with the struts to form plural longitudinal lumens, the overhangs cooperating with each other to form, on the outer surface of the drain, segments of a segmented, closed curve with gaps between the segments providing plural longitudinal grooves for fluid communication between the wound and a respective lumen, the grooves sized to inhibit tissue from growing therein and debris from passing therethrough.

18. The wound drain catheter system according to claim 17, wherein at least one lumen in the drain is closed from the suction device and supplies medication to the wound.

* * * * *